United States Patent [19]

Chan et al.

[11] Patent Number: 4,558,037
[45] Date of Patent: Dec. 10, 1985

[54] CARDIOVASCULAR COMPOSITION

[75] Inventors: Chi-Chung Chan, Kirkland; Anthony W. Ford-Hutchinson, Beaconsfield, both of Canada

[73] Assignee: Merck & Co., Inc., Rahway, N.J.

[21] Appl. No.: 617,293

[22] Filed: Jun. 4, 1984

[51] Int. Cl.$^4$ ............................................. A61K 37/00
[52] U.S. Cl. ..................................................... 514/20
[58] Field of Search ................. 260/112.5 R; 546/188; 549/12; 424/275; 514/20

[56] References Cited

U.S. PATENT DOCUMENTS

| | | | |
|---|---|---|---|
| 4,052,511 | 10/1977 | Cushman et al. | 546/221 |
| 4,129,571 | 12/1978 | Ondetti et al. | 546/188 |
| 4,154,960 | 5/1979 | Ondetti et al. | 260/112.5 R |
| 4,237,160 | 12/1980 | Hamel et al. | 424/275 |
| 4,334,077 | 6/1982 | Belanger et al. | 549/12 |
| 4,374,829 | 2/1983 | Harris et al. | 260/112.5 R |
| 4,394,515 | 7/1983 | Rokach et al. | 549/12 |
| 4,424,355 | 1/1984 | Belanger et al. | 546/35 |
| 4,435,579 | 3/1984 | Belanger et al. | 549/12 |

OTHER PUBLICATIONS

J. D. Pearson, et al., Thrombasis Research, 29, 115-124 (1983).
K. M. Mullane, et al., Eur. J. Phar., 66, 355-365 (1980).
C. C. Chan, et al., J. Pharmacol. Expt. Ther., 229, 276-282 (1984).

*Primary Examiner*—Delbert R. Phillips
*Attorney, Agent, or Firm*—Salvatore C. Mitri; Michael C. Sudol

[57] ABSTRACT

A cardiovascular composition is disclosed which comprises either dibenzo-thiepin derivatives alone or the combination of dibenzo-thiepin derivatives and angiotensin converting enzyme (ACE) inhibitors. These compositions represent a novel therapeutic approach to thromboembolic disease in man.

12 Claims, No Drawings

CARDIOVASCULAR COMPOSITION

BACKGROUND OF THE INVENTION

The present invention is directed toward a cardiovascular composition containing either an antithrombotic agent alone or the combination of an antithrombotic agent and an antihypertensive agent; more specifically, an angiotensin converting enzyme inhibitor.

Antihypertensive agents are known (see e.g., U.S. Pat. No. 4,129,571, U.S. Pat. No. 4,154,960, U.S. Pat. No. 4,052,511, U.S. Pat. No. 4,374,829). A particularly preferred class of these compounds are those disclosed in U.S. Pat. No. 4,374,829.

The class of antithrombotic agents used in the present invention are compounds known to be useful in the treatment of allergies; e.g., allergic asthma (see e.g., U.S. Pat. No. 4,394,515, U.S. Pat. No. 4,282,365, U.S. Pat. No. 4,263,207, U.S. Pat. No. 4,237,160, U.S. Pat. No. 4,334,077, U.S. Pat. No. 4,424,355, U.S. Pat. No. 4,435,579 and South African Pat. No. 78/4231). A particularly preferred class of these compounds are those disclosed in U.S. Pat. Nos. 4,237,160; 4,424,355 and 4,435,579 and South African Pat. No. 78/4231.

U.S. Pat. No. 4,237,160 discloses that dibenzo-thiepins are useful prostaglandin antagonists in reducing platelet aggregation; however, there is no disclosure or suggestion that these dibenzo-thiepin derivatives would be useful as thromboxane antagonists in reducing the formation of thrombi.

It has been discovered that these preferred antithrombotic compounds, administered either alone or in combination with the preferred antihypertensive agents, produce enhanced antithrombotic effects.

Thus, the compositions of this invention are useful in the treatment and/or prevention of thromboembolic diseases, particularly arterial thrombosis which has been reported to be initiated by injury of the blood vessel wall [J. F. Mustard, et al. *Drugs*, 9, 19–76 (1975); J. C. McGiff, *Adv. Intern. Med.*, 25, 199–216 (1980)].

SUMMARY OF THE INVENTION

A cardiovascular composition containing either an antithrombotic dibenzo-thiepin compound alone or said dibenzo-thiepin compound in combination with an angiotensin converting enzyme (ACE) inhibitor. It has been found that the dibenzo-thiepin compounds, when used alone, are useful thromboxane antagonists in reducing the formation of thrombi and that co-administration of the dibenzo-thiepin compounds with ACE inhibitor compounds potentiates the inhibition of arterial thrombosis.

DETAILED DESCRIPTION OF THE INVENTION

An embodiment of the invention is a cardiovascular composition useful for treating arterial thrombosis which comprises: (i) an antithrombotic dibenzo-thiepin compound generally represented by the formula

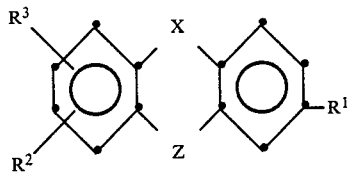

wherein:

X is a hydrocarbon group of $C_1$–$C_4$, straight chain or branched, saturated or unsaturated, optionally containing O, N or CO;

Z is S, SO, $SO_2$, CO, $CR^4R^5$ wherein $R^4$ and $R^5$ taken together form the group $=O$ or $=CHR^6$ wherein $R^6$ is hydrogen or phenyl;

$R^1$ is a member selected from the groups consisting of:

(a) 5-tetrazolyl, 5-tetrazolylmethyl, and

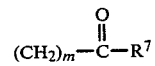

wherein m is an integer of from 0 to 4 and $R^7$ is a member selected from the group consisting of hydroxy, loweralkoxy, N,N-diloweralkylaminoloweralkoxy, hydroxyloweralkoxy, carboxyloweralkoxy, amino, N-loweralkylamino, N,N-diloweralkylamino, loweralkylsulfonylamino, carboxyloweralkylamino, carboxamidoloweralkylamino, 2-imino-3-methylthiazolidine; loweracyloxyloweralkoxy or (5-methyl-2-oxo-1,3-dioxolen-4-yl)methoxy;

(B) —CHO, —CH=$NR^8$ or

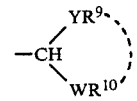

wherein $R^8$ is a member selected from the group consisting of hydrogen, loweralkyl, aryl, hydroxy, loweralkoxy, loweracyloxy, amino or loweralkylamino; Y and W are each independently oxygen, sulfur or $NR^9$; and $R^9$ and $R^{10}$ are each independently hydrogen or loweralkyl or may be joined to form a ring of 5–8 members;

—$(CH_2)_n$—$OR^{11}$ wherein n is 0–4 and $R^{11}$ is a member selected from the hydrogen loweracyl, loweralkylaminoacyl, loweralkylcarboxy, loweralkylcarboxamido, loweralkylcarboxamidoacyl or loweracyloxyloweralkyl;

$R^2$ and $R^3$ can each independently be hydrogen, halogen (F, Cl, Br or I), nitro, loweralkyl, amino, N-loweralkylamino, N,N-diloweralkyl amino, loweralkanoyl, hydroxy, loweralkoxy, lower acyloxy, loweralkylthio, trifluoromethylthio, loweralkylsulfinyl, loweralkylsulfonyl, trifluoromethyl, or $R^2$ and $R^3$, when bonded to adjacent carbon atoms, can be joined to form a 5- or 6-membered hydrocarbon ring which can optionally contain a double bond, a carbonyl group, or a hydroxyl group; and, the pharmaceutically acceptable salts thereof.

A further embodiment of the invention is a cardiovascular composition useful for treating arterial thrombosis which comprises: (1) the antithrombotic dibenzo-thiepin Formula I compound defined above; and, (ii) an angiotensin converting enzyme (ACE) inhibitor compound which is a member of the group: carboxyalkyl dipeptide derivatives; captopril [1-(3-mercapto-2-methyl-1-oxopropyl)-L-proline]; 2-[N-(S)-1-ethoxycarbonyl-3-phenylpropyl)-S-alanyl]-cis, endo-2-azabicyclo[3,3,0]octane-3(S)-carboxylic acid; N-((S)-1-ethoxycarbonyl-3-phenylpropyl)-L-alanyl-N-(2-indanyl)-glycine; 1-(N-[(S)-1-ethoxycarbonyl-3-phenylpropyl]-L-alanyl)-cis,synoctahydro-(H-indole-2-S)-carboxylic acid; 2-(N-[(S)-1-ethoxycarbonyl-3-phenylpropyl]-L-alanyl)-1,2,3,4-tetrahydroiso-isoquinoline-3(S)-carboxylic acid; and, 1-carboxymethyl-3(S)-(1(S)-ethoxycarbonyl-3-phenylpropylamino)-2,3,4,5-tetrahydro-1H[1]-benzazepine-2-one.

In particular the class of ACE inhibitors which have been found to have a potentiating effect when used in combination with the dibenzo-thiepin. Formula I compounds are those disclosed in U.S. Pat. No. 4,374,829, which also discloses methods for their preparation and which patent is incorporated herein by reference and which compounds are generally represented by the formula:

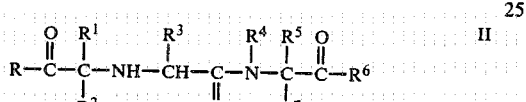

wherein
R and $R^6$ are the same or different and are
 hydroxy,
 lower $C_1$–$C_8$ alkoxy;
 lower $C_1$–$C_8$ alkenoxy;
 dilower $C_1$–$C_8$ alkylamino lower $C_1$–$C_8$ alkoxy (dimethylaminoethoxy);
 acylamino lower $C_1$–$C_8$ alkoxy (acetyl aminoethoxy);
 acyloxy lower $C_1$–$C_8$ alkoxy (pivaloyloxymethoxy);
 aryloxy, wherein the aryl is $C_6$ or $C_{10}$ such as phenoxy;
 arlower $C_1$–$C_8$ alkoxy, such as benzyloxy;
 substituted aryloxy or substituted arlower-$C_1$–$C_8$ alkoxy wherein the aryl is $C_6$ or $C_{10}$ and the substituent is methyl, halo or methoxy;
 amino;
 lower $C_1$–$C_8$ alkylamino;
 dilower $C_1$–$C_8$ alkylamino;
 hydroxyamino;
 arlower $C_1$–$C_8$ alkylamino wherein the aryl group is $C_6$–$C_{10}$ such as benzylamino;
$R^1$
 is hydrogen;
 hydrocarbon of from 1 to 20 carbon atoms which include branched and unsaturated (such as allyl) groups;
 $C_3$–$C_{10}$ cycloalkyl;
 substituted lower $C_1$–$C_8$ alkyl wherein the substituent can be halo, hydroxy, lower $C_1$–$C_8$ alkoxy, aryloxy wherein the aryl is $C_6$–$C_{10}$ such as phenoxy, amino, dilower $C_1$–$C_8$ alkylamino, acylamino such as acetamido and benzamido, arylamino wherein the aryl is $C_6$ or $C_{10}$, guanidino, imidazolyl, indolyl, mercapto, lower $C_{1-8}$ alkylthio, arylthio wherein the aryl is $C_6$ or $C_{10}$ such as phenylthio, carboxy or carboxamido, carbolower $C_{1-8}$ alkoxy;
aryl of $C_6$–$C_{10}$ such as phenyl or naphthyl;
 substituted aryl of $C_6$–$C_{10}$ such as phenyl wherein the substituent is lower $C_1$–$C_8$ alkyl, lower $C_1$–$C_8$ alkoxy or halo;
 unsubstituted or substituted arloweralkyl, arloweralkenyl, heteroarlower alkyl, or heteroarlower alkenyl, wherein aryl groups are $C_6$ or $C_{10}$, the alkyl groups are $C_2$–$C_8$, and the heteroatoms are one of O, N or S and the the substituent(s) is halo, dihalo, lower $C_1$–$C_8$ alkyl, hydroxy, lower $C_1$–$C_8$ alkoxy, amino, aminomethyl, acylamino (acetylamino or benzoylamino) dilower $C_1$–$C_8$ alkylamino, lower $C_1$–$C_8$ alkylamino, carboxyl, halolower $C_1$–$C_8$ alkyl, cyano or sulfonamido;
 arlower $C_1$–$C_8$ alkyl or heteroarlower $C_1$–$C_8$ alkyl wherein the aryl group is $C_6$ or $C_{10}$ and the heteroatom is one of O, N or S, substituted on the alkyl portion by amino or acylamino (acetylamino or benzoylamino);
$R^2$ and $R^7$ are the same or different and are hydrogen or lower $C_1$–$C_8$ alkyl;
$R^3$ is hydrogen, lower $C_1$–$C_8$ alkyl, phenyl lower $C_1$–$C_8$ alkyl, aminomethyl phenyl lower $C_1$–$C_8$ alkyl, hydroxy phenyl lower $C_1$–$C_8$ alkyl, hydroxy lower $C_1$–$C_8$ alkyl, acylamino lower $C_1$–$C_8$ alkyl (such as benzoylamino lower $C_1$–$C_8$ alkyl, acetylamino lower $C_1$–$C_8$ alkyl), amino lower $C_1$–$C_8$ alkyl, dimethylamino lower $C_1$–$C_8$ alkyl, halo lower $C_1$–$C_8$ alkyl, guanidino lower $C_1$–$C_8$ alkyl, imidazolyl lower $C_1$–$C_8$ alkyl, indolyl lower $C_1$–$C_8$ alkyl, mercapto lower $C_1$–$C_8$ alkyl, lower $C_1$–$C_8$ alkyl thio lower $C_1$–$C_8$ alkyl;
$R^4$ is hydrogen or lower $C_1$–$C_8$ alkyl;
$R^5$ is hydrogen, lower $C_1$–$C_8$ alkyl, phenyl, phenyl lower $C_1$–$C_8$ alkyl, hydroxy phenyl lower $C_1$–$C_8$ alkyl, hydroxy lower $C_1$–$C_8$ alkyl, amino lower $C_1$–$C_8$ alkyl, guanidino lower $C_1$–$C_8$ alkyl, imidazolyl lower $C_1$–$C_8$ alkyl, indolyl lower $C_1$–$C_8$ alkyl, mercapto lower $C_1$–$C_8$ alkyl or lower $C_1$–$C_8$ alkyl thio lower $C_1$–$C_8$ alkyl; or,
$R^4$ and $R^5$ may be connected together to form an alkylene bridge of from 2 to 4 carbon atoms, an alkylene bridge of from 2 to 3 carbon atoms and one sulfur atom, an alkylene bridge of from 3 to 4 carbon atoms containing a double bond or an alkylene bridge as above substituted with hydroxy, lower $C_1$–$C_8$ alkoxy, lower $C_1$–$C_8$ alkyl or dilower $C_{1-8}$ alkyl;
and, the pharmaceutically acceptable salts thereof.

Preferred antithrombotic dibenzo-thiepin compounds of Formula I are those wherein: Z, $R^2$, $R^3$ and $R^1$ are as defined above except that n in $R^1$ is 0; and X is $CH_2O$, $OCH_2$, $CH_2CH_2$ or $CH=CH$.

More preferred are those antithrombotic dibenzo-thiepin compounds of Formula I wherein:
X is $CH_2O$, $OCH_2$, $CH_2CH_2$ or $CH=CH$;
Z is S, SO, or $SO_2$;
$R^1$ is $CO_2H$, $CH=O$ or $CH_2OH$;
n is 0; and,
$R^2$ and $R^3$ are as defined above.

Still more preferred antithrombotic dibenzo-thiepin compounds of Formula I are those wherein:
X is $CH_2O$, $OCH_2$, $CH_2CH_2$ or $CH=CH$;
Z is SO or $SO_2$;
$R^1$ is $CO_2H$, $CH=O$ or $CH_2OH$;
n is 0; and,
$R^2$ and $R^3$ are as defined above.

Most preferred are those antithrombotic dibenzo-thiepin compounds of Formula I wherein:
X is $CH=CH$;

Z is SO or SO$_2$;
R$^1$ is CO$_2$H or CH$_2$OH;
R$^2$ and R$^3$ are each independently hydrogen or halogen (F, Cl, Br or I); and,
n is 0.

Preferred ACE inhibitor compounds of Formula II are those wherein:

R and R$^6$ can each independently be hydroxy, lower alkoxy, lower alkenoxy, arloweralkyloxy, amino, diloweralkylamino lower alkoxy, acylamino lower alkoxy or acyloxy lower alkoxy;

R$^1$ is
hydrogen, alkyl of from 1 to 20 carbon atoms, including branched, cyclic and unsaturated alkyl groups;
substituted lower alkyl wherein the substituent is halo, hydroxy, lower alkoxy, aryloxy, amino, loweralkylamino, diloweralkylamino, acylamino, arylamino, guanidino, imidazoyl, indolyl, mercapto, loweralkylthio, arylthio, carboxy, carboxamido or carbolower alkoxy;
phenyl;
substituted phenyl wherein the substituent is lower alkyl, lower alkoxy or halo;
arloweralkyl or heteroaryloweralkyl arloweralkenyl or heteroarloweralkenyl, substituted arloweralkyl, substituted heteroarylloweralkyl, substituted arloweralkenyl or substituted heteroarloweralkenyl;
wherein the substituent is halo or dihalo lower alkyl, hydroxy, lower alkoxy, amino, aminomethyl, acylamino, diloweralkylamino, loweralkylamino, carboxyl, halo alkyl, cyano or sulfonamido;
arloweralkyl or heteroarloweralkyl substituted on the alkyl portion by amino or acylamino;

R$^2$ and R$^7$ are hydrogen;
R$^3$ is lower alkyl, amino lower alkyl, imidazolyl, lower alkyl, halo lower alkyl;
R$^4$ and R$^5$ are joined to form an alkylene bridge of from 2 to 4 carbon atoms or an alkylene bridge of from 2 or 3 carbon atoms and one sulfur atom or an alkylene bridge of from 2 to 3 carbon atoms and one sulfur atom or an alkylene bridge of from 3 to 4 carbon atoms containing a double bond or an alkylene bridge of from 3 to 4 carbon atoms containing a double bond or an alkylene bridge as above substituted with hydroxy, lower alkoxy or lower alkyl;

or the pharmaceutically acceptable salts thereof wherein said aryl is a member selected from the group consisting of phenyl or naphthyl and said heteroaryl is a member selected from the group consisting of pyridyl, thienyl, furyl, indolyl, benzthienyl, imidazoyl, or thiazolyl.

More preferred are those antihypertensive compounds of Formula II wherein:

R and R$^6$ can each independently be hydroxy, lower alkoxy, lower alkenoxy, arloweralkyloxy, amino, diloweralkylamino lower alkoxy, acylamino lower alkoxy or acyloxy lower alkoxy;

R$^1$ is alkyl having from 1-8 carbon atoms, substituted lower alkyl wherein the alkyl group has 1-5 carbon atoms and the substituent is amino, arylthio, aryloxy or arylamino, aralkyl or heteroaralkyl wherein the alkyl portion has 1-3 carbon atoms, substituted aralkyl or heteroaralkyl wherein the alkyl groups have 1-3 carbon atoms and the substituent(s) is halo, dihalo, amino, aminoalkyl, hydroxy, lower alkoxy or lower alkyl;

R$^2$ and R$^7$ are hydrogen;
R$^3$ is lower alkyl or amino lower alkyl;

R$^4$ and R$^5$ can be joined together through the carbon and nitrogen atoms to which they are attached to form a ring of the formula:

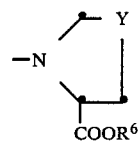

wherein Y is CH$_2$, S, or CH—OCH$_3$ or the pharmaceutically acceptable salts thereof wherein said aryl is a member selected from the group consisting of phenyl or naphthyl and said heteroaryl is a member selected from the group consisting of pyridyl, thienyl, furyl, indolyl, benzthienyl, imidazoyl or thiazolyl.

Still more preferred antihypertensive compounds of Formula II are those wherein:

R and R$^6$ can each independently be hydroxy, lower alkoxy, aralkyloxy;
R$^2$ and R$^7$ are hydrogen;
R$^3$ is methyl, aminoloweralkyl;
R$^4$ and R$^5$ are joined through the carbon and nitrogen atoms to form proline, 4-thiaproline or 4-methoxyproline and;
R$^1$ is alkyl having from 1-8 carbon atoms, substituted lower alkyl wherein the alkyl group has 1-5 carbon atoms and the substituent is amino, arylthio or aryloxy, aralkyl or heteroaralkyl wherein the alkyl portion has 1-3 carbon atoms, substituted aralkyl or heteroaralkyl wherein the alkyl groups have 1-3 carbon atoms and the substituent(s) is halo, dihalo, amino, aminoalkyl, hydroxy, lower alkoxy or lower alkyl;

and the pharmaceutically acceptable salts thereof wherein said aryl is a member selected from the group consisting of phenyl or naphthyl and said heteroaryl is a member selected from the group consisting of pyridyl, thienyl, furyl, indolyl, benzthienyl, imidazoyl or thiazolyl.

Examples of Formula I compounds are:
(a) dibenzo[b,f]thiepin-3-carboxylic acid;
(b) dibenzo[b,f]thiepin-3-carboxylic acid-5-oxide;
(c) dibenzo[b,f]thiepin-3-carboxylic acid-5,5-dioxide;
(d) 3-(5-tetrazolyl)dibenzo[b,f]thiepin-5,5-dioxide;
(e) 3-(5-tetrazolyl)dibenzo[b,f]thiepin;
(f) 3-(5-tetrazolyl)dibenzo[b,f]thiepin-5-oxide;
(g) 10,11-dihydrodibenzo[b,f]thiepin-3-carboxylic acid;
(h) 10,11-dihydrodibenzo[b,f]thiepin-3-carboxylic acid-5-oxide;
(i) 10,11-dihydrodibenzo[b,f]thiepin-3-carboxylic acid-5,5-dioxide;
(j) 10,11-dihydro-3-(5-tetrazolyl)dibenzo[b,f]thiepin;
(k) 10,11-dihydro-3-(5-tetrazolyl)dibenzo[b,f]thiepin-5-oxide;
(l) 10,11-dihydro-3-(5-tetrazolyl)dibenzo[b,f]thiepin-5,5-dioxide;
(m) 3-hydroxymethyldibenzo[b,f]thiepin;
(n) 3-hydroxymethyldibenzo[b,f]thiepin-5-oxide;
(o) 3-hydroxymethyldibenzo[b,f]thiepin-5,5-dioxide;
(p) 8-fluoro-3-hydroxymethyldibenzo[b,f]thiepin;
(q) 8-fluoro-3-hydroxymethyldibenzo[b,f]thiepin-5-oxide;
(r) 8-fluoro-3-hydroxymethyldibenzo[b,f]thiepin-5,5-dioxide;
(s) 3-hydroxymethyl-10,11-dihydrodibenzo[b,f]thiepin;
(t) 3-hydroxymethyl-10,11-[b,f]thiepin-5-oxide;

(u) 3-hydroxymethyl-10,11-dihydrodibenzo[b,f]thiepin-5,5-dioxide;
(v) 8-fluoro-3-hydroxymethyl-10,11-dihydrodibenzo[b,f]thiepin;
(w) 8-fluoro-3-hydroxymethyl-10,11-dihydrodibenzo[b,f]thiepin-5-oxide;
(x) 8-fluoro-3-hydroxymethyl-10,11-dihydrodibenzo[b,f]thiepin-5,5-dioxide;
(y) (−) 7- or 8-fluorodibenzo[b,f]thiepin-3-carboxylic acid-5-oxide;
(z) (+) 7- or 8-fluorodibenzo[b,f]thiepin-3-carboxylic acid-5-oxide; and
the like.

Examples of Formula II compounds are:
(i) N-(1-carboxy-3-phenylpropyl)-L-alanyl-L-proline;
(ii) N-(1-ethoxycarbonyl-3-phenylpropyl)-L-alanyl-L-proline;
(iii) N-(1-ethoxycarbonyl-4-methylpentyl)-L-alanyl-L-proline;
(iv) N-(1-carboxy-5-aminopentyl)-L-alanyl-L-proline;
(v) N-α-(1-carboxy-3-phenylpropyl)-L-lysyl-L-proline;
(vi) N-α-(1-ethoxycarbonyl-3-phenylpropyl)-L-lysyl-L-proline;
(vii) N-α-[1-carboxy-3-(3-indolyl)-propyl]-L-lysyl-L-proline;
(viii) N-α-[1-carboxy-3-(4-chlorophenyl)-propyl]-L-lysyl-L-proline;
(ix) N-α-[1-carboxy-2-phenylthioethyl]-L-lysyl-L-proline;
(x) N-α-[1-carboxy-3-(4-chlorophenyl)-propyl]-L-lysyl-trans-4-methoxy-L-proline;
(xi) N-α-[1-carboxy-5-aminopentyl]-L-lysyl-L-proline;
(xii) N-α-(1-carboxy-3-phenylpropyl)-L-ornithyl-L-proline;
(xiii) ethyl N-(1-ethoxycarbonyl-3-phenylpropyl)-L-alanyl-L-prolinate hydrochloride;
(xiv) N-[1-(ethoxycarbonyl)-3-(4-imidazolyl)propyl]-L-alanyl-L-proline.
(xv) N-[1-carboxy-3-(4-imidazolyl)propyl]-L-lysyl-L-proline;
(xvi) N-(1(S)-carboxy-3-phenylpropyl)-L-alanyl-L-proline;
(xvii) N-(1(S)-ethoxycarbonyl-3-phenylpropyl)-L-alanyl-L-proline maleate salt;
(xviii) N-α-(1(S)-carboxy-3-phenylpropyl)-L-lysyl-L-proline;
(xix) ethyl N-(1(S)-ethoxycarbonyl-3-phenylpropyl)-L-alanyl-L-prolinate hydrochloride;
(xx) N-α-(1(S)-ethoxycarbonyl-3-phenylpropyl)-L-lysyl-L-proline.

The above described Formula I compounds, their use, and methods for their preparation are disclosed in U.S. Pat. Nos. 4,237,160; 4,424,355; and 4,435,579 and South African Pat. No. 78/4231 all of which are incorporated herein by reference.

The above-described Formula II compounds, their use and the method of preparation thereof are disclosed in U.S. Pat. No. 4,374,829 which is incorporated herein by reference.

The resolution of certain Formula I compounds; i.e., dibenzo-thiepin sulfoxides; into their optically pure enantiomers is disclosed in U.S. Pat. Nos. 4,424,355 and 4,435,579 which have been incorporated herein by reference.

The combination composition of the invention can contain varying amounts of the Formula I (i) antithrombotic compound and Formula II (ii) antihypertensive compounds. The weight ratio of (i):(ii) can range from about 25 to 1; preferably from about 10 to 1. In addition to the active ingredients of (i) alone or of (i) and (ii) in combination, the compositions of the invention can also contain other conventional pharmaceutically acceptable compounding ingredients, as necessary or desired. Such ingredients are generally referred to as carriers or diluents. Conventional procedures for preparing such compositions in appropriate dosage forms can be utilized. Whatever the dosage form, it will contain a pharmaceutically effective amount of the present composition.

The present compositions can be administered orally or other than orally; e.g., parenterally, by insufflation, topically, rectally, etc.; using appropriate dosage forms; e.g., tablets, capsules, suspensions, solutions, and the like, for oral administration; suspension emulsions, and the like, for parenteral administration; solutions for intravenous administration; and ointments, transdermal patches, and the like, for topical administration.

Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparation. Tablets containing the active ingredient in admixture with non-toxic pharmaceutically acceptable excipients may also be manufactured by known methods. The excipients used may be for example, (1) inert diluents such as calcium carbonate, sodium carbonate, lactose, calcium phosphate or sodium phosphate; (2) granulating and disintegrating agents such as corn starch, or alginic acid; (3) binding agents such as starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in U.S. Pat. Nos. 4,256,108; 4,160,452; and 4,265,874 to form osmotic therapeutic tablets for controlled release.

In some cases, formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, for example peanut oil, liquid paraffin, or olive oil.

Aqueous suspensions normally contain the active materials in admixture with excipients suitable for the manufacture of aqueous suspensions. Such excipients may be
(1) suspending agents such as sodium carboxymethylcellulose, methylcellulose, hydroxypropylmethylcellulose, sodium alginate, polyvinylpyrrolidone, gum tragacanth and gum acacia;
(2) dispersing or wetting agents which may be
  (a) a naturally-occurring phosphatide such as lecithin,
  (b) a condensation product of an alkylene oxide with a fatty acid, for example, polyoxyethylene stearate,
  (c) a condensation product of ethylene oxide with a long chain aliphatic alcohol, for example, heptadecaethyleneoxycetanol, (d) a condensation product of ethylene oxide with a partial ester derived from a fatty acid and a hexitol such as polyoxyethylene sorbitol monooleate, or (e) a condensation product of ethylene oxide with a partial ester derived from a fatty acid and a hexitol anhydride, for example polyoxyethylene sorbitan monooleate.

The aqueous suspensions may also contain one or more preservatives, for example, ethyl or n-propyl p-hydroxybenzoate; one or more coloring agents; one or more flavoring agents; and one or more sweetening agents such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an antioxidant such as ascorbic acid.

Dispersible powders and granules are suitable for the preparation of an aqueous suspension. They provide the active ingredient in admixture with a dispersing or wetting agent, a suspending agent and one or more preservatives. Suitable dispersing or wetting agents and suspending agents are exemplified by those already mentioned above. Additional excipients, for example, those sweetening, flavoring and coloring agents described above may also be present.

The pharmaceutical compositions of the invention may also be in the form of oil-in-water emulsions. The oily phase may be a vegetable oil such as olive oil or arachis oils, or a mineral oil such as liquid paraffin or a mixture thereof. Suitable emulsifying agents may be (1) naturally-occurring gums such as gum acacia and gum tragacanth, (2) naturally-occurring phosphatides such as soy bean and lecithin, (3)esters or partial esters derived from fatty acids and hexitol anhydrides, for example, sorbitan monooleate, (4) condensation products of said partial esters with ethylene oxide, for example, polyoxyethylene sorbitan monooleate. The emulsions may also contain sweetening and flavoring agents.

Syrups and elixirs may be formulated with sweetening agents, for example, glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

A composition of the invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compositions of the invention are employed.

Treatment dosage for human beings can be varied as necessary. Generally, daily dosages of the composition of the invention can range from about 6000 to about 200 mg; preferably, from about 6000 to about 1000 mg.

The amount of active ingredient that may be combined with the carrier materials to produce a single dosage form will vary depending upon the host treated and the particular mode of administration. For example, a formulation intended for oral administration may contain from 5 mg to 5 gm of active agents compounded with an appropriate and convenient amount of carrier material which may vary from about 5 to about 95 percent of the total composition. Dosage unit forms will generally contain between from about 200 mg to about 6000 mg of active ingredients.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

The composition of this invention inhibits platelet accumulation at the damaged endothelial surface via the dibenzo-thiepin compound. This inhibitory effect is potentiated by the presence of the antihypertensive compound.

Thus, the compositions of the invention are useful in treating thrombosis and are also of value in the management of acute and chronic congestive heart failure.

In vivo testing of the composition of this invention in test animals (rabbits) has demonstrated that this composition is pharmaceutically effective in decreasing platelet-related arterial thrombic formation.

To demonstrate the potentiation of the antihypertensive compound on the anti-thrombotic dibenzo-thiepin compound comprising the combination composition of the invention, the effect of these compounds on test animals (rabbits) was determined separately and then in combination. The effect of a different class of antihypertensive agents singly and in combination with the dibenzo-thiepin compound of the invention was also determined for comparative purposes. The results obtained and the methods employed are described in the following Example.

EXAMPLE

Methods

New Zealand white rabbits of either sex (2–3 kg) were anesthetized intramuscularly (i.m.) with ketamine hydrochloride (35 mg/kg) and xylazine hydrochloride (5 mg/kg) and were ventilated with room air following tracheotomy. Anesthesia induced by this method lasts approximately 1 hour and sodium pentobarbital at 0.1 mg/kg/min was given intravenously (i.v.) thereafter. Nine mL of blood was collected from an indwelling catheter in the jugular vein for preparation and labelling of platelets with [111]Indium oxinate by the method described in detail by C. C. Chan, et al. [*J. Pharmacol.*

Expt. Ther., 229, 276–282, (1984)]. The labelled platelets were then injected back into the same rabbit intravenously. Thirty minutes after the injection, one of the carotid arteries was stimulated at 1–2 milliamperes (mA) for 2 minutes by means of a curved tip platinum electrode, followed after 20 minutes by excision of the stimulated and a posterior non-stimulated segment of carotid artery for determination of tissue radioactivity (expressed as counts per minute (cpm)/mg tissue). Platelet accumulation was assessed by the ratio of tissue radioactivity of the stimulated versus the non-stimulated segment. Histological confirmation of thrombi formation using this model has been reported by R. G. Hermann, et al. [*Platelets and Thrombosis*, 203–221, University Park Press, Baltimore (1974)] and M. J. Randall, et al. [*Br. J. Clin Pharmacol.*, 15, 495–565 (1983)]. An anti-thrombotic compound of the invention, i.e., an oxodibenzo-thiepin compound, (1 mg/kg, i.v.) and/or an angiotensin converting enzyme (ACE) inhibitor compound of the invention (0.5 mg/kg, i.v.) were administered immediately after the first carotid artery sections had been removed. A second stimulation, identical to the first, was performed on the contralateral carotid artery 15 minutes after drug treatment. In other experiments, a dibenzo-thiepin compound of the invention (1 mg/kg, i.v.) and the ganglionic blocking agent hexamethonium (5 mg/kg, i.v.) were given 5 minutes before the vasodilator hydralazine (1 mg/kg, i.v.) followed 15 minutes later by the second stimulation. Hexamethonium and hydralazine were co-administered in order to induce a drop in systemic blood pressure without a reflex increase in heart rate.

Plasma levels of immunoreactive-6-ketoprostaglandin $F_{1\alpha}$ ($PGF_{1\alpha}$) a stable metabolite of prostaglandin $I_2$ were determined in separate experiments using a $^{125}I$-radioimmunoassay (RIA) kit (New England Nuclear). Rabbits were surgically prepared as described above and, in addition, a polyethylene catheter, inside diameter size of 160, (PE 160) was inserted in one of the carotid arteries for blood sampling. The following protocol was used: electrical stimulation (3 mA, 2 minutes) of the intact carotid artery was performed 30 minutes after the rabbit had been stabilized, followed by withdrawal of the first blood sample (i.e., the resting value). A dibenzo-thiepin compound of the invention (1 mg/kg, i.v.) was administered immediately after blood sampling and 15 minutes later a second stimulation was performed on the same artery but at a different site. A second blood sample was then withdrawn followed by administration of an ACE inhibitor compound of the invention (0.5 mg/kg i.v.). Fifteen minutes later, the carotid artery was stimulated again (at a third site) and the last blood sample obtained. All blood samples, each of 2 mL, were withdrawn 4 to 5 minutes after electrical stimulation and were treated with the anticoagulant, ethylenediaminetetraacetic acid (EDTA) (1.8 mg/mL) and the prostaglandin synthetase inhibitor indomethacin (20 μl/ml) to block the synthesis of prostaglandin $I_2$ during handling of the blood sample. Plasma was obtained by centrifugation (1000 g, 2 minutes) and assayed without prior extraction and purification. In separate experiments, the order of administration of the dibenzothiepin and ACE inhibitor compounds of the invention was reversed to examine the effect of the ACE inhibitor compound alone. Time-matched vehicle control experiments were also conducted in which the administration of vehicles and sampling of blood were carried out in an identical time frame as the previous two experiments.

Drugs

All drug doses referred to were used as the free base. The representative dibenzo-thiepin compound of the invention employed was 3-hydroxymethyldibenzo[b,f]-thiepin-5,5-dioxide, hereinafter referred to as HDTD, and the representative ACE inhibitor compound of the invention employed was 1-(N-[1-(ethoxycarbonyl)-3-phenyl-propyl]-L-alanyl]-L-proline 1-ethylester hereinafter referred to as Enalapril. HDTD was dissolved in 50% polyethylene glycol (PEG) (mol. wt. 200) v/v in distilled water. Other commercially available drugs employed were: hexamethonium, hydrochloride, hydralazine, ketamine hydrochloride, sodium pentobarbital, and xylazine hydrochloride. $^{111}$Indium oxine was obtained from Byk-Mallinckrodt Ltd. (Petten, Holland) and was adjusted to pH 7.3 according to the manufacturer's instruction.

Results:

Potentiation of the inhibitory effect of HDTD by Enalapril

In eight vehicle-treated rabbits (0.1 mL/kg, 50%, (v/v) PEG in distilled water), tissue radioactivity of the stimulated and non-stimulated carotid segments during the first stimulation were 275±86 cpm/mg and 99±65 cpm/mg (means±standard error of mean (SEM)) respectively, resulting in a ratio of 4.9±1.1, this ratio being identified as $S_1$. Corresponding tissue cpm of the stimulated and non-stimulated segments during the second stimulation were 485±215 cpm/mg and 48±14 cpm/mg (means±SEM), yielding a ratio of 9.8±1.5, this ratio being identified as $S_2$.

Table I below shows the effects of different therapeutic treatments upon the accumulation of radioactive platelets at the site of electrical stimulation. Results are expressed as the percentage change in the tissue cpm ratio, i.e., $(S_2-S_1)/S_1$. This procedure accounts for the spontaneous changes in tissue cpm ratio between the two stimulations in the vehicle control group. As can be seen in Table I, HDTD produced a significant inhibition of platelet accumulation as has been previously described by C. C. Chan et al. [*J. Pharmacol. Expt. Ther.*, (1984)]. In contrast, Enalapril had no effect on platelet accumulation. However, when both compounds were administered together, there was a significant (p 0.05) potentiation of the inhibitory effect of HDTD.

TABLE I

| Percent Change in Tissue Radioactivity ($S_2 - S_1/S_1$) | | |
|---|---|---|
| Compounds(s) | n Value | Mean ± SEM |
| (1) Vehicle[a] | 8 | 157 ± 52 |
| (2) HDTD[b] (1 mg/kg) | 7 | 19 ± 15 |
| (3) 50% PEG Enalapril (0.5 mg/kg) | 4 | 201 ± 10 |
| (4) HDTD[b] [c] (1 mg/kg) Enalapril (0.5 mg/kg) | 9 | −(31 ± 12) |
| (5) HDTD[b] (1 mg/kg) hexamethonium (5 mg/kg) hydralazine (1 mg/kg) | 4 | 12 ± 10 |

[a] 50% v/v PEG in water (0.1 ml/kg)
[b] p < 0.05 vs. vehicle
[c] p < 0.05 vs. HDTD alone

Cardiovascular effects of Enalapril and HDTD in the Rabbit

Because it has been reported that Enalapril lowers blood pressure in several animal models of experimental hypertension [C. S. Sweet et al., Fed. Proc., 42, 167–170 (1983) and C. S. Sweet et al., Eur. J. Pharmacol., 76, 167–176 (1981)], it was necessary to examine in separate experiments whether Enalapril and HDTD produced effects upon blood pressure and heart rate in this model. In particular, it was important to determine whether the cardiovascular effects of the HDTD/Enalapril combination could account for the observed changes in platelet accumulation. As shown in Table II below, a combination of HDTD and Enalapril decreased blood pressure (a reduction of 14±3 mm Hg) and heart rate substantially in anesthetized rabbits. The hypotensive effect was mainly attributable to Enalapril because HDTD by itself had no significant cardiovascular actions (blood pressure before and after treatment with HDTD was 40±6 mm Hg and 39±3 mm Hg, respectively, n=6). In the group treated with Enalapril only, blood pressure before and after treatment was 54±7 mm Hg and 29±4 mm Hg respectively (p 0.05, n=5, a decrease of 25±9 mm Hg). Thus, HDTD inhibited rather than potentiated the hypotensive action of Enalapril. A combination of hexamethonium and hydralazine, which act by a different mechanism than Enalapril; i.e., by non-specific vasodilation, also lowered blood pressure to a similar extent to that observed for HDTD and Enalapril (Table II). However, there is no evidence for synergism in platelet accumulation experiments where HDTD was given together with hexamethonium and hydralazine as shown in Table I above.

TABLE II
Cardiovascular Effects of HDTD, Enalapril, Hexamethonium, and Hydralazine in Anesthetized Rabbits

| | | Basal | | 15 Minutes After Treatment | |
|---|---|---|---|---|---|
| Compounds[a] | n | Heart Rate (bpm) | Mean Blood Pressure (mm Hg) | Heart Rate (bpm) | Mean Blood Pressure (mm Hg) |
| (1) HDTD (1 mg/kg) Enalapril (0.5 mg/kg) | 5 | 231 ± 15 | 45 ± 1 | 187 ± 10 | 31 ± 4[c] |
| (2) HDTD (1 mg/kg) Hexamethonium (5 mg/kg) Hydralazine (1 mg/kg) | 4 | 218 ± 1 | 55 ± 3 | 221 ± 7 | 44 ± 4[b] |

[a]administered intravenously
[b]p < 0.05 vs. corresponding basal value
[c]p < 0.01 vs. corresponding basal value

Radioimmunoassay of plasma levels of 6-keto-PGF$_{1\alpha}$

A small but non-significant increase in plasma levels of immunoreactive-6-keto-PGF$_{1\alpha}$ in anesthetized rabbits was observed after administration of either HDTD or Enalapril as shown in Table III below wherein the mean and SEM of immunoreactive-6-keto-PGF$_{1\alpha}$ levels in 3 blood samples for 3 groups of rabbits with different treatments was determined. Treatment A was a time-matched vehicle control; treatment B employed HDTD followed by Enalapril; and, treatment C employed Enalapril followed by HDTD. As can be seen, the combination of both compounds, regardless of the order of administration, significantly increased plasma levels of immunoreactive-6keto-PGF$_{1\alpha}$. This increase was not observed in the time-matched vehicle control animals.

TABLE III
Effects of HDTD and/or Enalapril on Plasma Levels of 6-Keto-PGF$_{1\alpha}$

| Treatment | Compounds(s) | n Value | Basal | Treatment Compound(s) |
|---|---|---|---|---|
| A | — | 4 | 857 ± 284 | — |
| | PEG[a] | | | 767 ± 112 |
| | Saline | | | 980 ± 235 |
| B | — | 7 | 335 ± 97 | |
| | HDTD[b] | | | 669 ± 262 |
| | HDTD[b] + Enalapril[c] | | | 1081 ± 376[d] |
| C | — | 5 | 515 ± 137 | |
| | Enalapril[c] | | | 904 ± 289 |
| | HDTD[b] + Enalapril[c] | | | 1448 ± 422[d] |

[a]PEG = polyethylene glycol
[b]1 mg/kg
[c]0.5 mg/kg
[d]p < 0.05 vs. basal value in same treatment group.

As can be seen from the results obtained in the foregoing example, endothelial damage at the site of injury such as that induced by electrical stimulation results in platelet adhesion-aggregation at the injury site and release of platelet derived mediators including throboxane A$_2$ (TXA$_2$). TXA$_2$ may initiate secondary platelet aggregation leading to potentiation of thrombi formation. It has been demonstrated previously by C. C. Chan, et al. [J. Pharmacol. Expt. Ther., 229, 276-282, (1984)] that the TXA$_2$ antagonist HDTD selectively inhibits prostanoid-mediated platelet aggregation in vitro in human platelets and in vivo in animal models. As demonstrated above, Enalapril significantly potentiates the inhibition of arterial thrombi formation by HDTD in rabbits which is of particular significance in light of recent interest expressed in the treatment of hypertension and cardiac failure with angiotensin converting enzyme (ACE) inhibitors [A. Zanchetti et al., Am. J. Cardiol., 49, 1381–1579 (1982); G. P. Hodsman et al., Br. Med. J., 285, 1697–1699 (1982); H. J. Dargie et al. [Br. Heart J., 49, 305–308 (1983)].

What is claimed is:

1. A cardiovascular composition useful for treating thrombosis comprising a pharmaceutically effective carrier; an antithrombotically effective amount of a dibenzo-thiepin compound (i) having the formula:

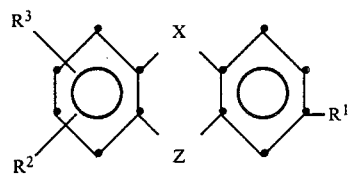

I wherein:
X is CH$_2$O, OCH$_2$, CH$_2$CH$_2$ or CH=CH;
Z is S, SO, or SO$_2$;
R$^1$ is CO$_2$H, CH=O, or CH$_2$OH;
R$^2$ and R$^3$ can each independently be hydrogen, halogen, nitro, loweralkyl, amino, N-loweralkylamino, N,N-diloweralkyl amino, loweralkanoyl, hydroxy, loweralkoxy, lower acyloxy, loweralkylthio, trifluoromethylthio, loweralkylsulfinyl, loweralkylsulfonyl, trifluoromethyl, or R$^2$ and R$^3$, when bonded to adjacent carbon atoms, can be joined to form a 5- or 6-membered hydrocarbon ring which can optionally contain a double bond, a carbonyl group, or a hydroxyl group;
and, an angiotensin converting enzyme inhibitor compound (ii) having the formula:

$$\text{R}-\overset{\overset{O}{\|}}{C}-\overset{\overset{R^1}{|}}{\underset{\underset{R^2}{|}}{C}}-NH-\overset{\overset{R^3}{|}}{CH}-\overset{\overset{|}{C}}{\underset{\underset{O}{\|}}{|}}-\overset{\overset{R^4}{|}}{N}-\overset{\overset{R^5}{|}}{\underset{\underset{R^7}{|}}{C}}-\overset{\overset{O}{\|}}{C}-R^6 \qquad II$$

wherein:
R and $R^6$ can each independently be hydroxy, lower alkoxy, lower alkenoxy, arloweralkyloxy, amino, diloweralkylamino lower alkoxy, acylamino lower alkoxy or acyloxy lower alkoxy;
$R^1$ is alkyl having from 1–8 carbon atoms, substituted lower alkyl wherein the alkyl group has 1–5 carbon atoms and the substituent is amino, arylthio, aryloxy or arylamino, aralkyl or heteroalkyl wherein the alkyl portion has 1–3 carbon atoms, substituted aralkyl or heteroalkyl wherein the alkyl groups have 1–3 carbon atoms and the substituent(s) is halo, dihalo, amino, aminoalkyl, hydroxy, lower alkoxy or lower alkyl;
$R^2$ and $R^7$ are hydrogen;
$R^3$ is lower alkyl or amino lower alkyl;
$R^4$ and $R^5$ can be joined together through the carbon and nitrogen atoms to which they are attached to form a ring of the formula:

$$-N\underset{COOR^6}{\overset{Y}{\diagdown\diagup}}$$

wherein Y is $CH_2$, S, or $CH-OCH_3$ or the pharmaceutically acceptable salts thereof wherein said aryl is a member selected from the group consisting of phenyl or naphthyl and said heteroaryl is a member selected from the group consisting of pyridyl, thienyl, furyl, indolyl, benzthienyl, imidazoyl or thiazolyl;
and, the pharmaceutically acceptable salts thereof, the weight ratio of said dibenzo-thiepin compound (i) to said angiotensin converting enzyme inhibitor compound (ii) in said composition being about 25 to 1.

2. The composition of claim 1 wherein said weight ratio is about 10 to 1.

3. The composition of claim 1 wherein said antithrombotic dibenzo-thiepin compounds of Formula I are those wherein:
X is $CH_2O$, $OCH_2$, $CH_2CH_2$ or $CH=CH$;
Z is SO or $SO_2$;
$R^1$ is $CO_2H$, $CH=O$ or $CH_2OH$; and,
$R^2$ and $R^3$ are as defined in claim 1.

4. The composition of claim 1 wherein the antithrombotic dibenzo-thiepin compounds of Formula I are those wherein:
X is $CH=CH$;
Z is SO or $SO_2$;
$R^1$ is $CO_2H$ or $CH_2OH$; and,
$R^2$ and $R^3$ are each independently hydrogen or halogen.

5. The composition of claim 1 wherein said angiotensin converting enzyme inhibitor compounds of Formula II are those wherein: R and $R^6$ can each independently be hydroxy, lower alkoxy, aralkyloxy;
$R^2$ and $R^7$ are hydrogen;
$R^3$ is methyl, aminoloweralkyl;
$R^4$ and $R^5$ are joined through the carbon and nitrogen atoms to form proline, 4-thiaproline or 4-methoxyproline and;
$R^1$ is alkyl having from 1–8 carbon atoms, substituted lower alkyl wherein the alkyl group has 1–5 carbon atoms and the substituent is amino, arylthio or aryloxy, aralkyl or heteroaralkyl wherein the alkyl portion has 1–3 carbon atoms, substituted aralkyl or heteroaralkyl wherein the alkyl groups have 1–3carbon atoms and the substituent(s) is halo, dihalo, amino, aminoalkyl, hydroxy, lower alkoxy or lower alkyl;
and the pharmaceutically acceptable salts thereof wherein said aryl is a member selected from the group consisting of phenyl or naphthyl and said heteroaryl is a member selected from the group consisting of pyridyl, thienyl, furyl, indolyl, benzthienyl, imidazoyl or thiazolyl.

6. The composition of claim 1 wherein said antithrombotic dibenzo-thiepin compound of Formula I is an optically pure enantiomer selected from the group:
(a) dibenzo[b,f]thiepin-3-carboxylic acid;
(b) dibenzo[b,f]thiepin-3-carboxylic acid-5-oxide;
(c) dibenzo[b,f]thiepin-3-carboxylic acid-5,5dioxide;
(d) 3-(5-tetrazolyl)dibenzo[b,f]thiepin-5,5-dioxide;
(e) 3-(5-tetrazolyl)dibenzo[b,f]thiepin;
(f) 3-(5-tetrazolyl)dibenzo[b,f]thiepin-5-oxide;
(g) 10,11-dihydrodibenzo[b,f]thiepin-3-carboxylic acid;
(h) 10,11-dihydrodibenzo[b,f]thiepin-3-carboxylic acid-5-oxide;
(i) 10,11-dihydrodibenzo[b,f]thiepin-3-carboxylic acid-5,5-dioxide;
(j) 10,11-dihydro-3-(5-tetrazolyl)dibenzo[b,f]thiepin;
(k) 10,11-dihydro-3-(5-tetrazolyl)dibenzo[b,f]thiepin-5-oxide;
(L) 10,11-dihydro-3-(5-tetrazolyl)dibenzo[b,f]thiepin-5,5-dioxide;
(m) 3-hydroxymethyldibenzo[b,f]thiepin;
(n) 3-hydroxymethyldibenzo[b,f]thiepin-5-oxide;
(o) 3-hydroxymethyldibenzo[b,f]thiepin-5,5-dioxide;
(p) 8-fluoro-3-hydroxymethyldibenzo[b,f]thiepin;
(q) 8-fluoro-3-hydroxymethyldibenzo[b,f]thiepin-5-oxide;
(r) 8-fluoro-3-hydroxymethyldibenzo[b,f]thiepin-5,5-dioxide;
(s) 3-hydroxymethyl-10,11-dihydrodibenzo[b,f]thiepin;
(t) 3-hydroxymethyl-10,11-dihydrodibenzo[b,f]thiepin-5-oxide;
(u) 3-hydroxymethyl-10,11-dihydrodibenzo[b,f]thiepin-5,5-dioxide;
(v) 8-fluoro-3-hydroxymethyl-10,11-dihydrodibenzo[b,f]thiepin;
(w) 8-fluoro-3-hydroxymethyl-10,11-dihydrodibenzo[b,f]thiepin-5-oxide; and,
(x) 8-fluoro-3-hydroxymethyl-10,11-dihydrodibenzo[b,f]thiepin-5,5-dioxide;
(y) −7-fluorodibenzo[b,f]thiepin-3-carboxylic acid-5-oxide;
(z) (+) 7-fluorodibenzo[b,f]thiepin-3-carboxylic acid-5-oxide;
(a,a) −8-fluorodibenzo[b,f]thiepin-3-carboxylic acid-5-oxide;
(b,b) (+) 8-fluorodibenzo[b,f]thiepin-3-carboxylic acid-5-oxide;

(c,c) 3-formyldibenzo[b,f]thiepin-5,5-dioxide;
(d,d) 6H-dibenzo[b,e]oxathiepin-2-carboxylic acid-5,5-dioxide; and,
(e,e) 6H-dibenzo[b,e]oxathiepin-9-carboxylic acid-5,5-dioxide; and, said angiotensin converting enzyme inhibitor compound II is selected from the group:
(i) N-(1-carboxy-3-phenylpropyl)-L-alanyl-L-proline;
(ii) N-(1-ethoxycarbonyl-3-phenylpropyl)-L-alanyl-L-proline;
(iii) N-(1-ethoxycarbonyl-4-methylpentyl)-L-alanyl-L-proline;
(iv) N-(1-carboxy-5-aminopentyl)-L-alanyl-L-proline;
(v) N-α-(1-carboxy-3-phenylpropyl)-L-lysyl-L-proline;
(vi) N-α-(1-ethoxycarbonyl-3-phenylpropyl)-L-lysyl-L-proline;
(vii) N-α-[1-carboxy-3-(3-indolyl)-propyl]-L-lysyl-L-proline;
(viii) N-α-[1-carboxy-3-(4-chlorophenyl)-propyl]-L-lysyl-L-proline;
(ix) N-α-[1-carboxy-2-phenylthioethyl]-L-lysyl-L-proline;
(x) N-α-[1-carboxy-3-(4-chlorophenyl)-propyl]-L-lysyl-trans-4-methoxy-L-proline;
(xi) N-α-[1-carboxy-5-aminopentyl]-L-lysyl-L-proline;
(xii) N-α-(1-carboxy-3-phenylpropyl)-L-ornithyl-L-proline;
(xiii) ethyl N-(1-ethoxycarbonyl-3-phenylpropyl)-L-alanyl-L-prolinate hydrochloride;
(xiv) N-[1-(ethoxycarbonyl)-3-(4-imidazolyl)propyl]-L-alanyl-L-proline; (xv) N-[1-carboxy-3-(4-imidazolyl)-propyl]-L-lysyl-L-proline; (xvi) N-(1(S)-carboxy-3-phenylpropyl)-L-alanyl-L-proline; (xvii) N-(1(S)-ethoxycarbonyl-3-phenylpropyl)-L-alanyl-L-proline; (xviii) N-(1(S)-ethoxycarbonyl-3-phenylpropyl)-L-alanyl-L-proline maleate salt; (xix) N-α-(1(S)-carboxy-3-phenylpropyl)-L-lysyl-L-proline; and, ethyl N-(1(S)-ethoxycarbonyl-3-phenylpropyl)-L-alanyl-L-prolinate hydrochloride; and,
(xx) N-α-(1(S)-ethoxycarbonyl-3-phenylpropyl)-L-lysyl-L-proline.

7. The composition of claim 6 wherein said dibenzothiepin compound of Formula I is a member selected from the group:
(c) dibenzo[b,f]thiepin-3-carboxylic acid-5,5-dioxide;
(o) 3-hydroxymethyldibenzo[b,f]thiepin-5,5-dioxide;
(y) −7-fluorodibenzo[b,f]thiepin-3-carboxylic acid-5-oxide;
(z) (+) 7-fluorodibenzo[b,f]thiepin-3-carboxylic acid-5-oxide;
(a,a) −8-fluorodibenzo[b,f]thiepin-3-carboxylic acid-5-oxide;
(b,b) (+) 8-fluorodibenzo[b,f]thiepin-3-carboxylic acid-5-oxide;
(c,c) 3-formyldibenzo[b,f]thiepin-5,5-dioxide;
(d,d) 6H-dibenzo[b,e]oxathiepin-2-carboxylic acid-5,5-dioxide; and,
(e,e) 6H-dibenzo[b,e]oxathiepin-9-carboxylic acid-5,5-dioxide; and,
said angiotensin converting enzyme inhibitor compound II is a member selected from the group consisting of:
N-(1(S)-ethoxycarbonyl-3-phenylpropyl)-L-alanyl-L-proline;
N(1(S)-carboxy-3-phenylpropyl)-L-alanyl-L-proline;
N-α-(1(S)-carboxy-3-phenylpropyl)-L-lysyl-L-proline; and,
the maleate salts of said angiotensin converting enzyme inhibitor compounds.

8. The composition of claim 6 wherein said dibenzothiepin compound of Formula I is dibenzo[b,f]thiepin-3-carboxylic acid-5,5-dioxide and said angiotensin converting enzyme inhibitor compound of Formula II is N-(1(S)-ethoxycarbonyl-3-phenylpropyl)-L-alanyl-L-proline.

9. The composition of claim 6 wherein said antithrombotic dibenzo-thiepin compound of Formula I is 3-hydroxymethyldibenzo[b,f]thiepin-5,5-dioxide and said angiotensin converting enzyme inhibitor compound of Formula II is N-(1(S)-ethoxycarbonyl-3-phenylpropyl)-L-alanyl-L-proline.

10. The composition of claim 6 wherein said antithrombotic dibenzo-thiepin compound of Formula I is dibenzo[b,f]thiepin-3-carboxylic acid-5,5-dioxide and said angiotensin converting enzyme inhibitor compound of Formula II is N-α-(1(S)-carboxy-3-phenylpropyl)-L-lysyl-L-proline.

11. The composition of claim 6 wherein said antithrombotic dibenzo-thiepin compound of Formula I is 3-hydroxymethyldibenzo[b,f]thiepin-5,5-dioxide and said angiotensin converting enzyme inhibitor compound of Formula II is N-α-(1(S)-carboxy-3-phenylpropyl)-L-lysyl-L-proline.

12. A method for treating thrombosis in a patient needing said treatment which comprising an administering an effective amount of the composition of claim 1.

* * * * *